United States Patent
Duric et al.

(10) Patent No.: US 9,518,966 B2
(45) Date of Patent: Dec. 13, 2016

(54) METHOD AND TEST DEVICE FOR FIELD CALIBRATION OF A GAS DETECTOR

(75) Inventors: Aleksandar Duric, Zug (CH); Harald Ebner, Baar (CH); Martin Forster, Jona (CH)

(73) Assignee: SIEMENS SCHWEIZ AG, Zurich (CH)

( * ) Notice: Subject to any disclaimer, the term of this patent is extended or adjusted under 35 U.S.C. 154(b) by 824 days.

(21) Appl. No.: 13/617,255

(22) Filed: Sep. 14, 2012

(65) Prior Publication Data
US 2013/0074575 A1   Mar. 28, 2013

(30) Foreign Application Priority Data
Sep. 16, 2011   (EP) ..................................... 11181594

(51) Int. Cl.
*G01N 33/00* (2006.01)
*G01N 27/416* (2006.01)
*G08B 29/22* (2006.01)

(52) U.S. Cl.
CPC ...... *G01N 33/0006* (2013.01); *G01N 27/4163* (2013.01); *G08B 29/22* (2013.01)

(58) Field of Classification Search
CPC .................. G01N 33/0006; G01N 27/4163
USPC ............................................... 73/1.03, 1.06
See application file for complete search history.

(56) References Cited

U.S. PATENT DOCUMENTS

| 5,659,125 A | 8/1997 | Ernst |
| 6,237,392 B1* | 5/2001 | Yu et al. ......................... 73/1.06 |
| 2006/0042353 A1* | 3/2006 | Marquis et al. ................ 73/23.2 |
| 2006/0156789 A1 | 7/2006 | Frank et al. |
| 2010/0326165 A1 | 12/2010 | Rauworth et al. |

FOREIGN PATENT DOCUMENTS

| DE | 102008015145 | 10/2009 |
| EP | 11181594 | 9/2011 |
| WO | 01/65211 | 9/2001 |

* cited by examiner

*Primary Examiner* — Hezron E Williams
*Assistant Examiner* — David Z Huang
(74) *Attorney, Agent, or Firm* — Slayden Grubert Beard PLLC

(57) ABSTRACT

A method and test devices are used for field calibration of gas detectors. Brand new gas detectors are used as measurement standards in field calibration. The brand new gas detectors are in this case either employed directly as working standards, in which case the regular calibration by a reference standard is dispensed with, since the brand new gas detectors are always deemed to be sufficiently accurate. Alternatively, the brand new gas detectors are employed directly, namely as sufficiently accurately calibrated reference standards for the reference gas sensors acting as working standards and incorporated into the test device. In both cases the measured values of the gas sensors in the gas detectors to be calibrated are fed back to a sufficiently calibrated system, namely either directly to at least one brand new gas detector as a working standard or else to a reference sensor of a calibrated test device.

1 Claim, 2 Drawing Sheets

METHOD AND TEST DEVICE FOR FIELD CALIBRATION OF A GAS DETECTOR

CROSS REFERENCE TO RELATED APPLICATIONS

This application claims the benefit of EP11181594, filed on Sep. 16, 2011 in the European Patent Office, the disclosure of which is incorporated herein in its entirety by reference.

BACKGROUND

The invention relates to the field calibration of gas detectors, in which the concentration of a reference gas is determined.

It is known for test devices to be recalibrated at regular intervals. This may be done by measuring the concentration of a reference gas. The reference gas concentration may be a known quantity of reference gas. Recalibration is done in the factory or in a special test laboratory. This procedure is complex and entails high costs, and is impractical for the test devices widely used in the field.

SUMMARY

One possible object is to simplify the field calibration of gas detectors. Another possible object is to ensure that a reference sensor of a test device used for field calibration, which itself is exposed to aging and environmental influences, gives correct measured values.

A central idea to the inventors' proposals is to use at least one brand new gas detector as a measurement standard, in other words as a comparison device for calibrating the gas detector in the field. It is thereby ensured that the sensitivity of the tested gas detectors in the field lies within a predefined range.

The term "gas detector" here refers to gas detectors and gas-smoke detectors, whereby a gas-smoke detector refers to a smoke detector that also measures a gas, and a gas detector refers to a gas detector that measures any gas. In particular the inventors' proposals relate to the field calibration of CO gas-smoke detectors, in other words smoke detectors which measure smoke and carbon monoxide, and/or CO gas detectors, in other words gas detectors which measure carbon monoxide. The proposals are however not restricted to carbon monoxide gas measuring detectors. Detectors which measure another gas or several gases are also included under the term "gas detector" used generally below, as are detectors which additionally comprise one or more further sensor arrangements, e.g. for temperature measurement.

The term "brand new" here refers to a newly produced, so far unused and hence also only insignificantly aged gas detector ("out of the box") which is of sufficient quality for calibration purposes. In other words "brand new" means that the sensitivity of the gas detector has changed only insignificantly since its last calibration, which took place when it was manufactured in the factory. "Brand new" also means a recalibrated or reworked gas detector which corresponds to a newly manufactured gas detector in respect of its suitability as a measurement standard.

The high-cost and impractical calibration of the test devices in the factory or in a special test laboratory is avoided in that either the field calibration is carried out with at least one test device which uses a brand new gas detector as a reference, or else the test device is calibrated before the field calibration using at least one brand new gas detector.

Expressed differently, the at least one second, brand new gas detector, the sensitivity of which is known, is used either as a working standard, namely as a reference gas sensor of the test device, or else as a reference standard for a working standard, in other words as a reference for the reference gas sensor of the test device.

The inventors' proposals in other words relate to the use of at least one second, brand new gas detector as a measurement standard, either in the calibration of a first gas detector or in the calibration of a test device which is used for calibrating a first gas detector. Two variant embodiments are possible here, which are described in greater detail below.

In the first variant embodiment, the method for calibrating the gas detector has the following steps: determination of the concentration of a reference gas by measurement with a gas sensor of the gas detector to be checked, determination of the concentration of the reference gas by measurement with the gas sensor of at least one second brand new gas detector acting as a working standard, determination of the deviation of the concentration determined during the measurement with the gas detector from the concentration determined during the measurement with the at least one second gas detector, and processing the determined deviation such that this is taken into account when the gas detector is used subsequently to correct a measurement of the gas concentration. The reference gas concentration may be an unknown concentration. Expressed differently, during the calibration a measurement procedure takes place to establish and document the deviation of the measured values of the gas detector to be calibrated from the measured values of the at least one second gas detector acting as a working standard. Additionally the determined deviation is taken into account when the gas detector is subsequently used to correct the measured values. To this end the determined deviation is processed, this entailing at least storage in a memory contained in the gas detector and/or transfer to a receiver, for example a corresponding database or a fire alarm control panel.

In this method calibration is not effected using a works standard, with which the gas sensors are calibrated during the manufacture of the fire alarms. However, the calibration is effected using at least one reference gas sensor, the accuracy of which approximates very closely to the works standard. As the brand new, calibrated second fire alarms are gradually built in by the test personnel in the field and thus new second gas detectors are constantly being drawn on as working standards for the field calibration, their sensitivity degradation is negligible.

The test device adapted to perform this method is characterized in that it is designed for a simultaneous measurement of the gas concentration by two or more gas detectors. The test device does not require its own reference gas sensor. Instead, the calibration electronics of the test device are designed such that they communicate with the at least one second gas detector and after a simultaneous reference measurement of the gas concentration of a reference gas by the first and the at least one second gas detector calibrate the gas detector to be calibrated with the at least one second gas detector as a working standard. The adapter embodied for two or more gas detectors is designed such that it ensures a uniform gas concentration at all connected gas detectors.

To this end either a common test volume is provided for the gas detectors or several test volumes isolated from one another which are associated with the respective gas detectors. In the simplest case the first gas detector to be checked is demounted and is laid together with the at least one second gas detector in a common test space of the test device which can be locked by a lid. In another embodiment, the test device has a connection adapter for at least two gas detectors. If the test device is correspondingly designed, for example if the adapter has corresponding sealing elements such as sealing lips or similar, it is also possible to check the first gas detector in the mounted state.

The calibration procedure either involves demounting the gas detector to be checked from its operating position and connecting it to the test device, or alternatively, in an embodiment, leaving the gas detector to be checked in its operating position. The test device is then designed such that it is ensured that the at least one second gas detector, just like the gas detector to be checked, is attached gas-tight to the test volume. In particular if the gas detector to be checked is to be calibrated in its operating position, it must additionally be ensured that both gas detectors are equally gas-tight on the side facing away from the reference gas supply line, to ensure an identical outflow behavior of the reference gas in both gas detectors.

In the second variant embodiment the actual calibration of the gas detector is in principle carried out in the same way as described in connection with the first variant, but with the difference that the test device with its own reference gas sensor is used as a working standard rather than the at least one second gas detector. The test device is however first calibrated with the second gas detector as a reference standard. In other words, the test device with a built-in reference gas sensor is first calibrated using the at least one second gas detector as a reference standard. The recalibrated test device then acts as a working standard for calibrating the first gas detector in the field. The calibration of the test device can be effected before each field calibration of a gas detector. The reference gas sensors in the test device can age arbitrarily. As they are always recalibrated before the field calibration, this is unimportant for the quality of the field calibration, as long as they have the minimum sensitivity and dynamics required for the intended use and normally predefined by standards. If this is no longer the case, they are replaced by new reference gas sensors.

This embodiment, in which the at least one second gas detector is used as a reference standard for a working standard, is in other words characterized in that at least one reference gas sensor of a test device is calibrated by at least one brand new second gas detector and that the first gas detector to be calibrated is calibrated by the at least one reference gas sensor. Both calibrations are carried out consecutively, the sequence of the measurements of the reference gas concentration on which the calibrations are based being of no importance.

The test device adapted to perform this method is characterized in that its adapter merely has to be designed to create a connection with a single gas detector, which greatly simplifies the design structure of the test device compared to the first embodiment. However, the test device now being used must have at least one reference gas sensor. The calibration electronics connected to the reference gas sensor are designed for communicating with the at least one second gas detector and for calibrating the first gas detector with the at least one second gas detector as a reference standard.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
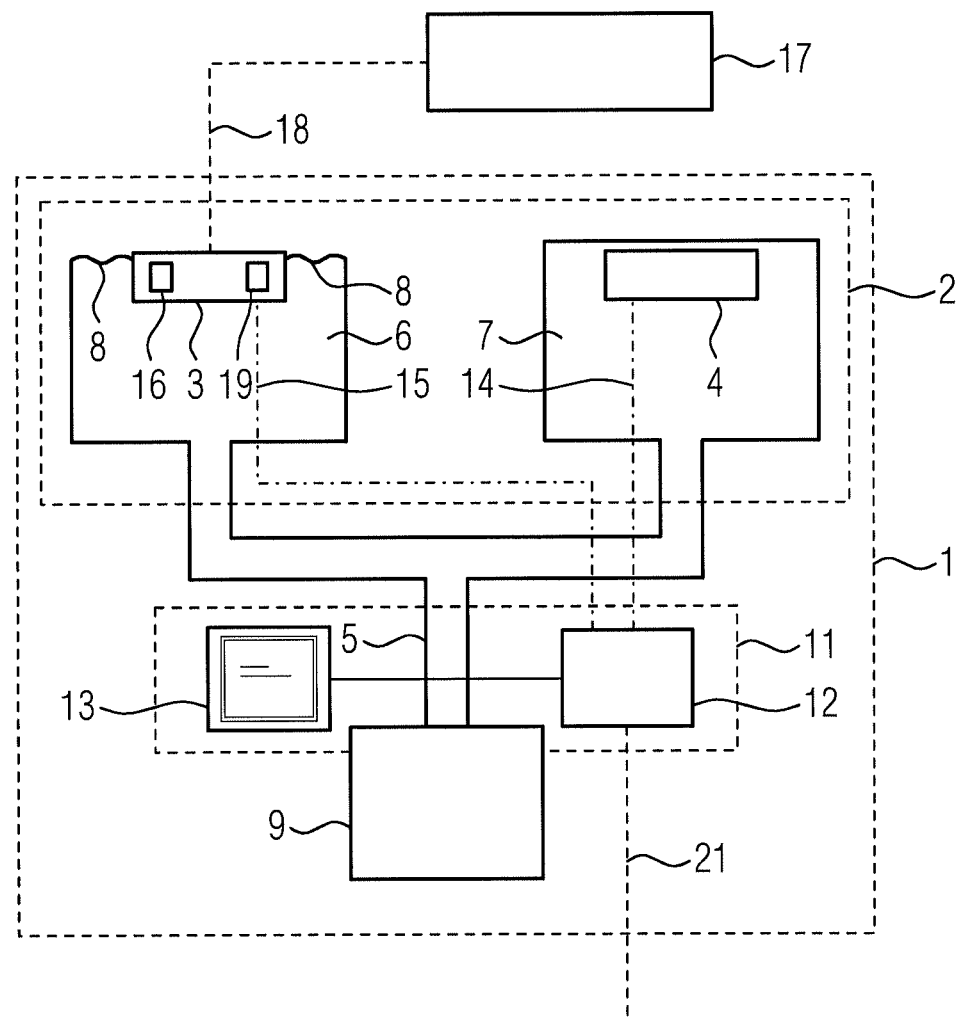
FIG. 1 shows a system for field calibration of gas detectors (first exemplary embodiment)

Reference will now be made in detail to the preferred embodiments of the present invention, examples of which are illustrated in the accompanying drawings, wherein like reference numerals refer to like elements throughout.

All figures show the proposals merely schematically and with its important components.

In a first exemplary embodiment shown in FIG. 1 a test device 1 for field calibration has an adapter 2 for accommodating two gas detectors 3, 4. Both a first gas detector 3 to be calibrated and a brand new, second gas detector 4 are exposed to an identical reference gas concentration. A symmetric distributor arrangement 5 ensures that in each case the same amount of reference gas flows into both the identical test volumes 6, 7.

The adapter part providing the first test volume 6 is placed over the first gas detector 3, which is still in its mounting position, and is sealed using circumferential sealing lips 8 attached to the adapter housing.

The adapter housing is designed, in the test volume 7 provided for the second gas detector 4, such that the second gas detector 4 connected to the adapter is located in a position which in respect of the inflow and throughflow ratios of the reference gas emulates the operating position of the first gas detector 3 or corresponds to such a position.

To provide the reference gas the test device 1 comprises a gas generator 9, for example in the form of a pressure cylinder, with the help of which an unknown amount of reference gas is generated and is fed into the test volume formed by the two partial volumes 6, 7.

The test device 1 further comprises calibration electronics 11 with an evaluation unit 12 and a display unit 13. The display unit 13 is designed to display the reference concentration measured by the second gas detector 4. The second gas detector 4 is connected to the calibration electronics 11 via a wired or wireless communication line 14.

The calibration of the gas detector 3 to be checked is preferably carried out as follows in the first exemplary embodiment: to check the first gas detector 3 located in its operating position the test device 1, to the adapter 2 of which the second, brand new gas detector 4 is already attached, is placed over the gas detector 3 to be checked, the sealing lips 8 made of rubber sealing the adapter 2, thereby creating a relatively gas-tight space in the interior of the adapter 2. An absolute gas-tightness is to be avoided, so that it is still possible for the reference gas to flow out. In a next step a determined, but unknown amount of reference gas is let into the two partial volumes 6, 7 connected to one another and associated with the gas detectors from the gas generator 9 via the distributor 5. Then both gas detectors 3, 4 measure the reference gas concentration. Based on the differences in the measurement results, the first gas detector 3 is calibrated. A calibration of this type is basically known to the person skilled in the art and hence is to be described only by way of example below.

The gas concentration measured by the second gas detector 4 is transmitted to the calibration electronics 11 and is displayed using the display unit 13 of the calibration electronics.

If there is a direct communication link between the first gas detector 3 and the test device 1, for example in the form of a wireless optical communication link 15, the first gas detector 3 transmits the gas concentration measured by it to the calibration electronics 11. The evaluation unit 12 of the calibration electronics immediately calculates, from the measurement results of the two gas detectors 3, 4, the sensitivity of the first gas detector 3 and saves the result in a storage space 16 provided for this in the first gas detector 3. The values previously stored there are overwritten in this case.

If there is no communication link between the first gas detector 3 and the test device 1, but only with a remote receiver 17, for example a fire alarm control panel, the first gas detector 3 sends the measured gas concentration to the remote receiver 17 via the existing connection, for example a bus system 18, which enables bidirectional communication. The gas detector 3 to be checked is in this case switched to a test mode before the start of calibration, for example by actuating a switch 19. The calibration electronics 11 are designed for such a case, such that the evaluation unit 12 likewise sends the measured gas concentration of the second gas detector 4 to the remote receiver 17, for which purpose a communication link 21 is provided. The information received is stored in the remote receiver 17 and from the ratio of the two measured concentrations a correction of the sensitivity of the first gas detector 3 is calculated and is sent via the existing communication link 15 to the first gas detector 3.

Thus either a correction of the aging-related measurement deviations can be effected directly in the first gas detector 3 or else a remote receiver 17 calculates the aging from the data received and takes this into account when assessing the measurement results, the latter mostly being practiced in systems in which a correction directly in the gas detector 3 is not permitted for safety reasons.

Other variants are possible using the previously described option of communication between gas detector 3 and control panel 17. For example, the gas detector 3 can communicate in a wired or wireless manner with the control panel 17 via the test device 1 or the gas detector 3 communicates with an upload database or generally with a higher-level management system via the test device 1, for example a system with detector calibration data management, which further communicates with the control panel 17.

Figure 2:
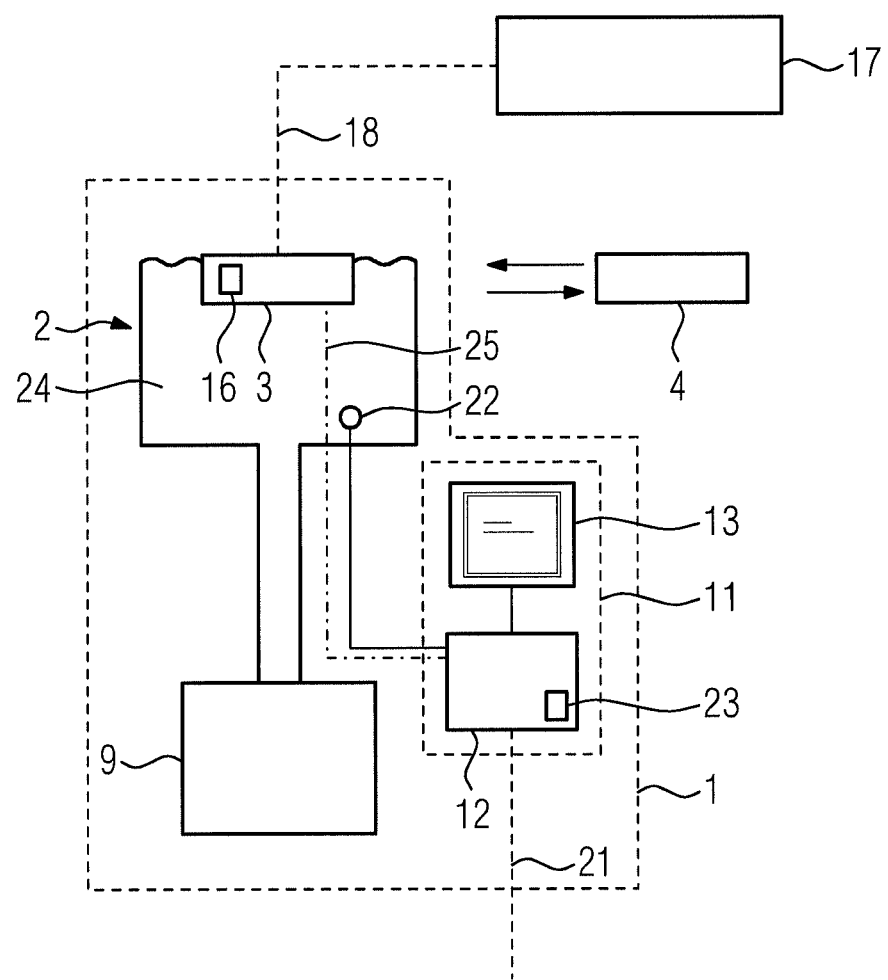
FIG. 2 shows a system for field calibration of gas detectors (second exemplary embodiment).

In the second exemplary embodiment shown in FIG. 2 the test device 1 has a less complex structure. In particular, the adapter 2 is embodied such that it can only be connected to one gas detector 3, 4 in each case.

The test device 1 in this case has one or more reference gas sensors 22, which measure the concentration of the reference gas in the test volume 24. The use of several sensors increases the reliability of the reference measurement in this case. It is especially advantageous if thanks to a modular structure it can be ensured that the reference sensors are easily interchangeable. However, this is only necessary if they have aged so much that they can no longer be returned to their original sensitivity.

In this exemplary embodiment the test device 1 has two operating modes and the calibration is preferably effected as follows: the adapter 2 is placed over the brand new gas detector 4 and the calibration electronics 11 are switched to "calibration of the reference sensor" mode, for example by actuating a switch 23 provided on the calibration electronics 11. Then an unknown amount of reference gas is fed into the interior of the adapter 2. The reference gas sensor 22 of the test device 1 measures the gas concentration of the reference gas and transmits the measurement results to the calibration electronics 11. At the same time the second gas detector 4 communicates via a communication link 25 with the test device 1 and sends the concentration of reference gas measured by it to the calibration electronics 11. The evaluation unit 12 automatically calculates the correction of the reference gas sensor 22 from the measurement results received and stores it in the memory of the test device's integrated reference gas sensor 22. Measured values and deviations can additionally be displayed using the display unit 13 of the calibration electronics 11. If the measurement is repeated with other reference devices, i.e. if several brand new gas detectors 4 are measured, the accuracy of the calibration can be increased. Following this, the reference gas sensor 22 of the test device 1 is calibrated.

To calibrate the gas detector 3 to be checked, the brand new gas detector 4 is isolated from the adapter 2 of the test device 1 and the gas detector 3 to be checked is connected to the adapter 2. Additionally the calibration electronics 11 are switched to "calibration of a gas detector" mode, for example again using the switch 23. This situation is illustrated in FIG. 2. Reference gas is then fed into the test volume 24.

The previously freshly calibrated reference gas sensor 22 in the test device 1 measures the gas concentration and transmits the measurement result to the calibration electronics 11 connected to the reference gas sensor 22. Then, as in the embodiment described above, the first gas detector 3 is checked and/or calibrated. For this, the evaluation unit 12 calculates the sensitivity of the first gas detector 3 from the measurement results of the two gas detectors 3, 4 and stores the result in a memory space 16 of the first gas detector 3 provided for this purpose and/or transmits the measurement results to a remote receiver 17 via the bus system 18 or another communication link. In this variant embodiment too, the communication options described above between gas detector 3 and test device 1 or between gas detector 3 and control panel 17 can be used.

It is advantageous that the sequence of the measurements is not compulsory. In another variant embodiment the measurements of the reference gas concentrations, on which the calibrations are based, are performed in a different sequence than just described. First the reference gas concentration is measured using the test device 1 and the gas detector 3 to be checked. Then the reference gas concentration is measured with the test device 1 and the second gas detector 4. From these measurement results, which are stored in the calibration electronics 11, the correction for the first gas detector 3 is calculated and is transmitted to the gas detector 3 wirelessly directly or via the control panel 17. The calibration of the reference gas sensor 22 of the test device 1 can in other words also be effected subsequently to the measurement with the gas detector to be checked 3. The sequence of the measurements is irrelevant for the calculation of the calibration.

The inventors propose a method and test devices 1 for field calibration of gas detectors 3. The method and devices utilize the basic idea of using brand new gas detectors 4 as measurement standards in field calibration. The brand new gas detectors 4 are in this case either employed directly as working standards, in which case the regular calibration by a reference standard is dispensed with, since the brand new gas detectors 4 are always deemed to be sufficiently accurate. Alternatively, the brand new gas detectors 4 are employed directly, namely as sufficiently accurately calibrated reference standards for the reference gas sensors 22 acting as working standards and incorporated into the test device 1. In both cases the measured values of the gas sensors in the gas detectors 3 to be calibrated are fed back to a sufficiently calibrated system, namely either directly to at least one brand new gas detector 4 as a working standard or else to a reference sensor 22 of a test device 1 calibrated using at least one such brand new gas detector 4.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV*, 69 USPQ2d 1865 (Fed. Cir. 2004).

The invention claimed is:

1. A test device for calibrating a first gas detector in the field, the test device comprising:
   a reference gas sensor;
   an adapter configured to connect to a second gas detector for calibrating the reference gas sensor and to connect to the first gas detector for calibrating the first gas detector, the second gas detector being a gas detector having a known calibration; and
   a switching device configured to switch an operating mode of the test device between a mode that calibrates the reference gas sensor using the second gas detector when the adapter is connected to the second gas detector and a mode that calibrates the first gas detector using the reference gas sensor when the adapter is connected to the first gas detector, wherein
   the adapter includes a seal that fits on both the first gas detector and the second detector such that in the mode that calibrates the reference gas sensor the adapter is sealed to the second gas detector and in the mode that calibrates the first gas detector the adapter is sealed to the first gas detector.

* * * * *